United States Patent
Vagos

(10) Patent No.: US 7,751,061 B2
(45) Date of Patent: Jul. 6, 2010

(54) NON-CONTACT APPARATUS AND METHOD FOR MEASURING A PROPERTY OF A DIELECTRIC LAYER ON A WAFER

(75) Inventor: Pedro Vagos, Bend, OR (US)

(73) Assignee: Nanometrics Incorporated, Milpitas, CA (US)

( * ) Notice: Subject to any disclaimer, the term of this patent is extended or adjusted under 35 U.S.C. 154(b) by 319 days.

(21) Appl. No.: 11/780,331

(22) Filed: Jul. 19, 2007

(65) Prior Publication Data

US 2008/0018882 A1    Jan. 24, 2008

Related U.S. Application Data

(60) Provisional application No. 60/832,722, filed on Jul. 20, 2006.

(51) Int. Cl.
G01B 11/02 (2006.01)
G01B 11/28 (2006.01)

(52) U.S. Cl. ........................ 356/504; 356/630

(58) Field of Classification Search ........... 356/503, 356/504, 630, 632
See application file for complete search history.

(56) References Cited

U.S. PATENT DOCUMENTS 4,555,767 A * 11/1985 Case et al. ............... 356/504
6,381,009 B1   4/2002 McGahan \* cited by examiner

*Primary Examiner*—Patrick J Connolly
(74) *Attorney, Agent, or Firm*—Silicon Valley Patent Group LLP

(57) ABSTRACT

Non-contact apparatus and methods for evaluating at least one of the DC (or RF) dielectric constant, the hardness, and Young's Modulus of a dielectric material on a microelectronic workpiece under process and for generating a correlation factor that relates a measured IR spectrum to at least one of the dielectric constant, the hardness, and Young's Modulus of the dielectric material. A specific example of a method comprises measuring a thickness of the dielectric material on the process workpiece, irradiating the process workpiece with an IR source, and collecting and measuring an IR spectrum from the process workpiece. The measured thickness and at least a portion of the measured IR spectrum from the process workpiece are used with the correlation factor to determine at least one of the dielectric constant, the hardness, and Young's Modulus of the dielectric material. The determined value from the correlation factor is then stored and/or displayed.

22 Claims, 5 Drawing Sheets

NON-CONTACT APPARATUS AND METHOD FOR MEASURING A PROPERTY OF A DIELECTRIC LAYER ON A WAFER

CROSS-REFERENCE TO RELATED APPLICATIONS

This application claims the benefit of U.S. Provisional Application No. 60/832,722, filed Jul. 20, 2006, entitled "Non-Contact Apparatus and Method for Measuring a Property of a Dielectric Layer on a Wafer", which is incorporated herein by reference.

TECHNICAL FIELD

The present invention relates to measuring a property of a dielectric layer on a microelectronic workpiece using IR spectroscopy and/or IR spectral ellipsometry. The property of the dielectric layer can be the direct current (DC) or radio frequency (RF) dielectric constant (k), the Young's Modulus (M), and the hardness (H).

BACKGROUND

Semiconductor devices, microelectronic devices, and other microfeature devices are typically manufactured on a workpiece having a large number of individual dies (e.g., chips). Each wafer undergoes several different procedures to construct the switches, capacitors, conductive interconnects and other components of a device. For example, a workpiece can be processed using lithography, implanting, etching, deposition, planarization, annealing, and other procedures that are repeated to construct a high density of features. One aspect of manufacturing microelectronic devices is forming dielectric layers at several different levels throughout the manufacturing process.

Dielectric layers are one of the primary components in integrated circuits. For example, high-k dielectric layers are used as the gates in transistors, and low-k dielectric layers are used to separate interconnect lines arranged in several levels of a microelectronic workpiece. Dielectric layers can also be used as masks in the fabrication processes, passivation layers, and/or cap layers. Dielectric layers are often formed by depositing a uniform layer of dielectric material, which has a matrix material that may be doped with some atoms or molecules. In several applications, the matrix material can be transformed using an activation energy, such as thermal energy, ultraviolet energy, or e-beam energy, to form pores within the matrix material. Nanoglass is also a porous dielectric material, but it is fabricated by a different process.

One aspect of manufacturing microelectronic devices is ascertaining certain properties of the dielectric layers. For example, the dielectric constant must be within a desired range for the dielectric layers to function properly. In the case of interlayer dielectrics or inter-metallization dielectric layers, it is typically desirable to have a lower k value to enable high-speed operation of the integrated circuits. For transistor gates, however, a higher k value is desired. The dielectric layers should also have a desired elasticity and hardness because if they are too hard or too soft they can compromise the performance of other fabrication processes. A soft dielectric layer, for example, may be crushed in subsequent chemical-mechanical planarization, cleaning, and/or packaging processes. As a result, it is necessary to evaluate the properties of the dielectric layers at several stages throughout fabricating integrated circuits.

One challenge of fabricating integrated circuits, however, is that conventional techniques for measuring properties of the dielectric layers may be inconvenient and may damage the wafers. For example, the DC (or RF) dielectric constant is conventionally measured by contacting the dielectric layer with an electrode and applying an electrical signal across the dielectric layer. The contact of the electrode may damage or contaminate the wafer. Similarly, the Young's Modulus and the hardness of the dielectric layer are conventionally measured using nano-tip indents that may similarly damage or contaminate the wafer. Therefore, it would be desirable to develop a non-contact method that measures a property of a dielectric layer using a suitable type of energy.

SUMMARY

In accordance with an embodiment of the present invention, at least one of the DC (or RF) dielectric constant, the hardness, and Young's Modulus of a dielectric material on a microelectronic workpiece under process is evaluated without the need to contact the workpiece. A specific example of a method comprises measuring a thickness of the dielectric material on the process workpiece, irradiating the process workpiece with an IR source, and collecting and measuring an IR spectrum from the process workpiece. The measured thickness and at least a portion of the measured IR spectrum from the process workpiece are used with a predetermined correlation factor to determine at least one of the dielectric constant, the hardness, and Young's Modulus of the dielectric material. The determined value from the correlation factor is then stored and/or displayed.

In another embodiment, a correlation factor that relates a measured IR spectrum to at least one of the DC (or RF) dielectric constant, the hardness, and Young's Modulus of the dielectric material is generated using a plurality of calibration wafers. The value at least one of the DC (or RF) dielectric constant, the hardness, and Young's Modulus of the dielectric material on individual calibration wafers is measured along with the thickness of the dielectric material on the individual calibration wafers. A test IR spectrum is collected from the individual calibration wafers to obtain a plurality of test IR spectra. A metric is then determined from the measured values, the thicknesses and the test IR spectra. The metric, which relates the measured IR spectrum with a value of at least one of the DC (or RF) dielectric constant, the hardness, and Young's Modulus of the dielectric material, is then stored as the correlation factor.

DETAILED DESCRIPTION

A. Overview

Figure 1:
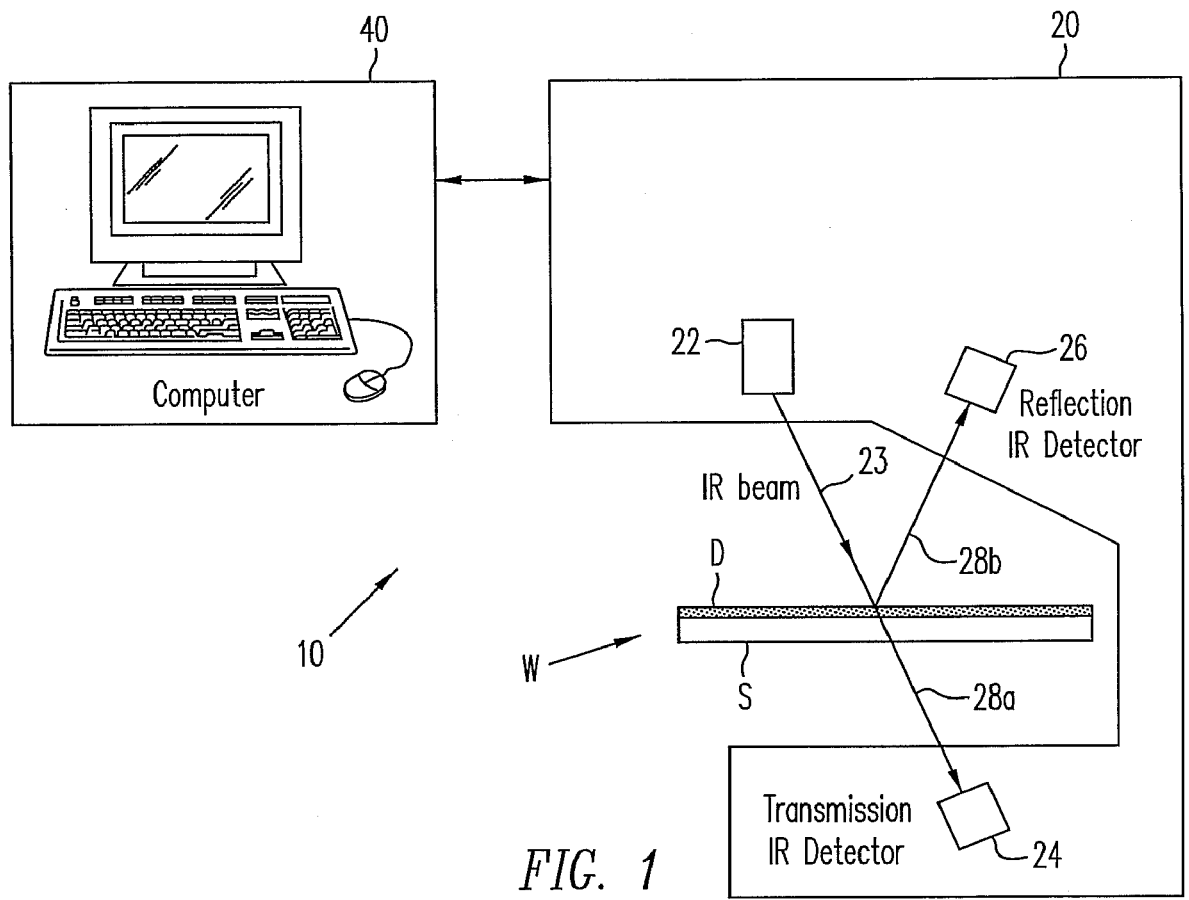
FIG. 1 is a schematic view of a system for measuring a property of a dielectric material on a workpiece in accordance with an embodiment of the invention.

The present invention is directed toward evaluating dielectric layers on microelectronic workpieces and other types of substrates without contacting the dielectric layers. Many applications of the present invention are directed toward measuring the DC (or RF) dielectric constant, the Young's Modulus and/or the hardness of porous dielectric layers and nanoglass layers on microfeature workpieces. Suitable workpieces include semiconductor workpieces, micromechanical workpieces, and/or optical workpieces. In semiconductor applications, the workpiece can be a silicon substrate, gallium arsenide substrate, or other suitable semiconductor materials (e.g., InP, SiC, etc.). Other materials, such as quartz or ceramics, may also be suitable workpieces. The dielectric layers can be any porous low-k dielectric material like Carbon Doped Silicon Oxide (CDO), Silica aerogel/exrogel (nanoglass), or other suitable dielectric materials.

One embodiment of the invention is a non-contact method for evaluating a property of a dielectric material on a microelectronic workpiece under process. A specific example of this method comprises measuring a thickness of the dielectric material on the process workpiece, irradiating the process workpiece with an IR source, and collecting an IR spectrum from the process workpiece. The method continues by inputting the measured thickness and at least a portion of the IR spectrum from the process workpiece into a predetermined correlation between IR spectra and the property of the dielectric material from calibration wafers. The method further includes outputting a value of the property for the dielectric material of the process workpiece from the correlation.

One specific embodiment of this method further comprises determining the correlation between the IR spectra and the property of the dielectric material using the calibration wafers. In this embodiment, the correlation is determined by providing a plurality of calibration wafers with the dielectric material, measuring an actual value of the property of the dielectric material on individual calibration wafers with an appropriate measuring device, and collecting a plurality of test IR spectra from individual calibration wafers using the IR spectrometer. The process for determining the correlation between IR spectra and the property of the dielectric material further includes measuring a thickness of the dielectric material on the calibration wafers, and determining a metric from the actual values of (a) the property of the dielectric material, (b) the test IR spectra, and (c) the thickness of the dielectric material on the individual calibration wafers. The metric relates the IR spectrum from workpieces like the calibration wafers with the property of the dielectric material. Suitable procedures for determining the metric include a sum of weighted IR bands, a sum of weighted IR bands using band curve fitting, principal components regression algorithms, partial least squares algorithms, and/or inverse least squares algorithms.

Many specific details of particular embodiments are set forth in the following description and the figures to provide a thorough understanding of these embodiments. The invention, however, may have additional embodiments that lack some of the details set forth in the detailed description section or include additional structures or processes. For example, the following detailed description describes several embodiments of the invention in the context of determining the RF dielectric constant of a porous silicon dioxide layer on a silicon substrate, but the invention is equally applicable to other types of workpieces with different types of substrates and dielectric layers. Moreover, it should be understood that the list of algorithms described herein to create the metric that correlates the IR spectrum of the dielectric material with the property of interest of that dielectric material is not exhaustive. Therefore, a person skilled in the art will understand that the present invention may have other embodiments in addition to or in lieu of the specific embodiments described below.

B. Embodiments of Apparatus and Methods for Evaluating Dielectric Layers

FIG. 1 is a schematic view of a system 10 for measuring a property of a dielectric material on a workpiece. The system 10 can include an IR spectrometer 20 having an IR source 22 that generates an IR beam 23 with a plurality of wavelengths and at least one IR detector. In the embodiment illustrated in FIG. 1, the IR spectrometer 20 includes a transmission IR detector 24 and/or a reflection IR detector 26. The IR beam 23 from the IR spectrometer 20 is directed towards a spot on a wafer W having a dielectric layer D on a substrate S. The transmitted IR beam 28a, which is the fraction of the IR beam that passes through the workpiece W, is detected by the transmission IR detector 24. The reflected IR beam 28b, which is the fraction of the IR beam that is reflected by the workpiece W, is detected by the Reflection IR detector 26. The IR spectrometer 20 measures and stores the records the transmission IR spectrum collected by the transmission IR detector 24 from the dielectric layer D on the workpiece W and/or the reflection IR spectrum collected by the reflection IR detector 26.

The system 10 further includes a computer 40 operatively coupled to the IR spectrometer 20. In operation, the IR spectrometer 20 sends the measured IR spectra, i.e., the transmission and/or reflection IR spectra, to the computer 40 along with an indication of the location of the workpiece W irradiated by the IR beam 23. The computer 40 includes a computer-operable medium, such as software and/or hardware, for performing a non-contact method that evaluates a property of the dielectric layer D on the workpiece W. The computer-operable medium, for example, includes instructions that cause the computer 40 to store in memory or output to a user interface, such as a display, the value of the property of the dielectric layer D based on a predetermined correlation factor between IR spectra and the property of the dielectric material that is stored in the computer 40. As explained in more detail below, the correlation between the IR spectra and the property of the dielectric layer D may be determined using calibration wafers to ascertain a metric that is computed by (a) the sum of weighted IR bands, (b) the sum of weighted IR bands using band curve fitting, (c) principal components regression algorithms, (d) partial least squares computations, and/or (e) inverse least squares computations.

Figure 2:
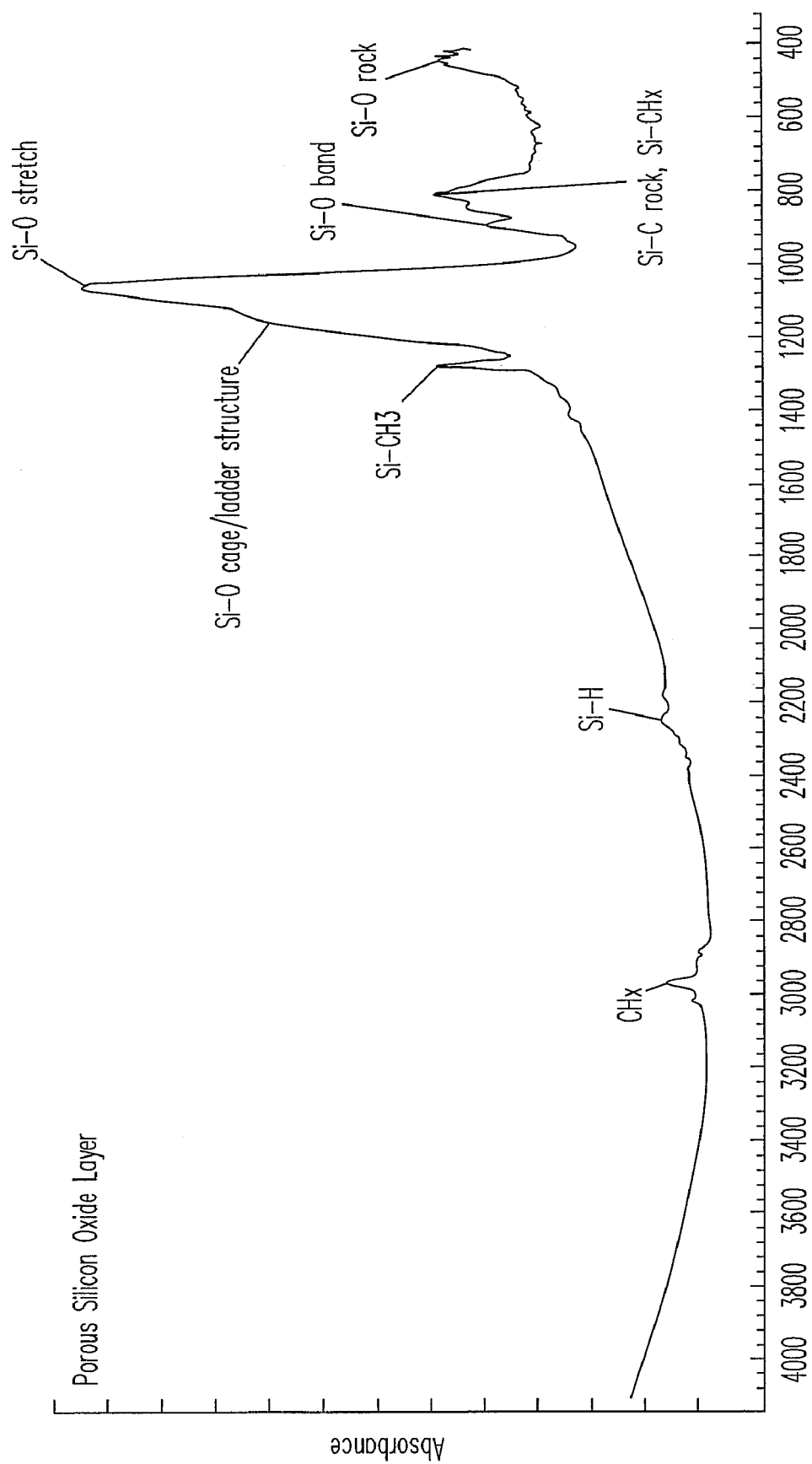
FIG. 2 is a graph illustrating an example of an IR spectrum from a dielectric layer.

FIG. 2 is a graph illustrating an example of a Transmission IR spectrum from a porous silicon oxide dielectric layer obtained, e.g., using the transmission IR detector 24. Infrared spectroscopy using such an IR spectrum is generally used to characterize the composition of some dielectric layers, such as the measurement of the concentration of fluorine in silicate glass (FSG) or the measurement of phosphorous and boron in boronphosphosilicate glass (BPSG), which is described, e.g., in U.S. Pat. No. 6,381,009, the entirety of which is incorporated herein by reference. The IR spectrum of any material is a signature of its molecular composition because the mid-IR photons interact primarily with matter by exciting the vibrational modes of its molecular bonds. The IR spectrum of a porous dielectric layer generally differs from the spectrum of the matrix material. Some of the IR bands are not from the matrix material itself, but rather from some residual molecules in the matrix material that are either free or bonded to the matrix material. Such residual molecules can be from porogens, solvents, surfactants or other "contaminants." The measured IR spectrum in FIG. 2 has a number of peaks that correspond to the residual "contaminants" molecular species bonded to the dielectric SiO2 matrix material. As such, IR spectroscopy has conventionally been used to determine the composition of dielectric layers as opposed to the DC (or RF) dielectric constant, Young's Modulus, or hardness.

One aspect of using the measured IR spectrum from the system 10 includes correlating measurements of a property of the dielectric material to the IR spectrum of that dielectric material acquired using a Fourier Transform Infrared Spectrometer (FTIR). In the case of measuring the DC (or RF) dielectric constant of porous dielectric films, previous studies focused on the correlation of the DC (or RF) dielectric constant to the ratio of areas of different IR bands. In particular, such previous studies used the IR bands associated with Si—CH$_3$ at 1410 cm$^{-1}$ and SiO at 1040 cm$^{-1}$. The methodology of using the coarse measured IR spectrum illustrated in FIG. 2 and the ratio of areas of the selected IR bands, however, did not provide sufficiently accurate correlations for most applications because of differences in the thickness and density of the dielectric layers on different wafers and the variation on the baselines and band shapes of the respective IR spectra, that limit its applicability. The system 10 and the methods of using the computer 40 in accordance with several embodiments of the present invention compensate for such limitations by determining a metric that correlates IR spectra to the RF dielectric constant or other property of the dielectric layer D in association with the thickness of the measured dielectric layer.

C. Non-Contact Methods for Measuring a Property of a Dielectric Layer

Figure 3:
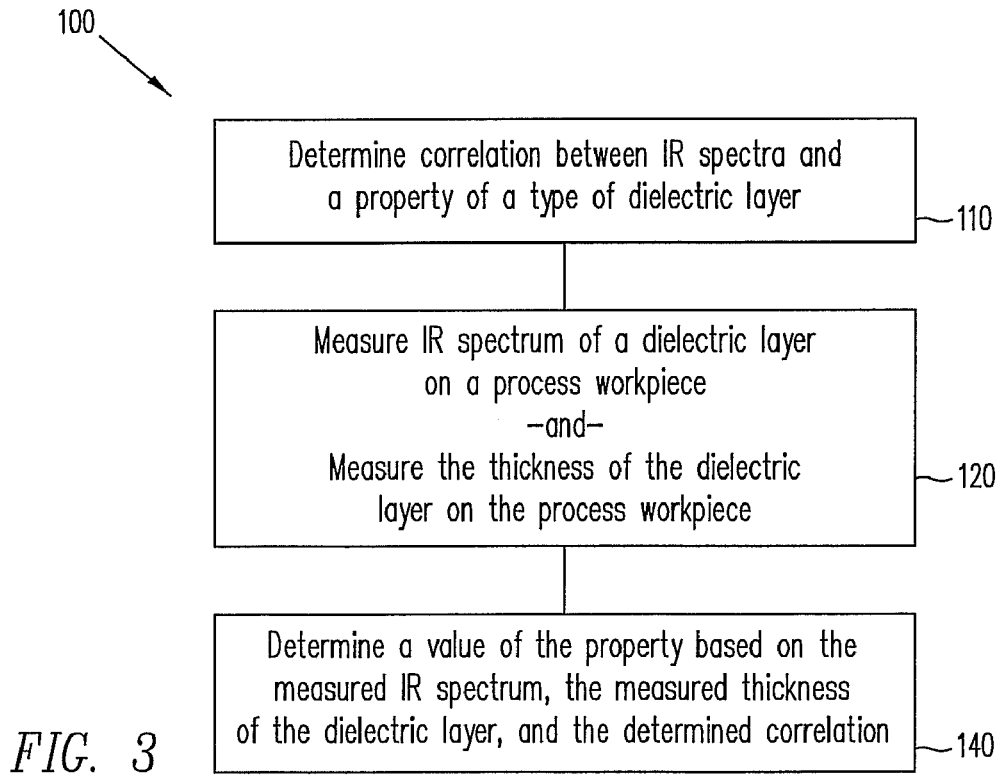
FIG. 3 is a flow chart of a non-contact method for evaluating a property of a dielectric layer on a microfeature workpiece in accordance with an embodiment of the invention.

FIG. 3 is a flow chart of a non-contact method 100 for evaluating a property of a dielectric layer on a microfeature workpiece in accordance with an embodiment of the invention. The method 100 includes a calibration phase 110 that involves determining a correlation factor between IR spectra and a property of the same type of dielectric material using calibration wafers and storing the calibration factors, e.g., in computer 40 to be used in the analysis of a dielectric layer on a process workpiece. The calibration phase 110 for a given type of dielectric material includes measuring the thicknesses of several dielectric layers and the values of at least one of the DC (or RF) dielectric constant, Young's Modulus, and hardness of the dielectric layers on a number of calibration wafers. An IR spectrum of each calibration wafer is recorded and then analyzed by a computer to determine the best metric for correlating the property of the dielectric layer with the type of IR spectra. Suitable methods for determining the correlation factor include calculating a metric according to (a) the sum of weighted IR bands, (b) the sum of weighted IR bands using band curve fitting, (c) principal components regression algorithms, (d) partial least squares algorithms, and/or (e) inverse least squares algorithms.

The method 100 further includes a measurement stage 120 in which the IR spectrum of an unknown sample or process workpiece is acquired using the same technique for collecting the IR spectra from the calibration wafers in the calibration phase 110 (FTIR or IR-SE in transmission or reflection mode, etc.). The IR spectrum is typically obtained using the IR spectrometer 20 described above with reference to FIG. 1. The measurement stage 120 also includes measuring the thickness of the dielectric layer on the process workpiece.

The IR spectra for the calibration phase 110 and the measurement stage 120 is preferably measured in the range 400 cm$^{-1}$ to 6000 cm$^{-1}$. The spectra can be recorded by using a Fourier Transform Infrared Spectrometer (FTIR), but it can also be obtained by using any other type of infrared spectrometer (e.g., dispersive IR spectrometers). The IR spectra can be acquired either in transmission mode using the transmission IR detector 24 or in reflection mode using the reflection IR detector 26. The analysis of the spectra acquired in the transmission mode is generally easier. If the spectra are collected in reflection mode, they can be used if the substrate is highly reflective and therefore the absorption bands of the low-k layer are detectable. Another possibility is to simulate a reflectance spectrum that fits the experimental reflectance spectrum using physical principles. The spectrum of the extinction coefficient or the spectrum of the imaginary part of the dielectric function can be obtained from such a simulated spectrum, and these can be input into a program that calculates a metric "X" that correlates with the DC (or RF) dielectric constant, Young's Modulus, and/or the hardness.

The IR spectra can also be recorded by using an Infrared Spectral Ellipsometer (IR-SE). In this case, the recorded spectra are the polarization $\Delta$ and $\Psi$ (or cos(A) and tan($\Psi$)) as a function of the wavenumber. From the $\Delta$ and $\Psi$ spectra, the extinction coefficient spectrum or the imaginary part of the dielectric function spectrum can be calculated and input into the program that calculates the metric that correlates with the DC (or RF) dielectric constant, Young's Modulus, and/or the hardness.

The method 100 further includes a determination stage 140 in which the measured thickness of the dielectric layer on the process workpiece and at least a portion of the measured IR spectrum of the dielectric layer on the process workpiece from the measurement stage 120 are input into the computer 40. The computer 40 uses the measured thickness and measured IR spectrum along with the predetermined correlation factor to determine the value of the desired property of the dielectric layer, i.e., the DC (or RF) dielectric constant, Young's Modulus, and hardness. The determination stage 140 further includes storing in memory and/or outputting to an appropriate user interface, such as a display, the value of the determined property of the dielectric layer from the predetermined correlation between IR spectra and the property of interest from the calibration phase 110.

The calibration phase 110 has several embodiments that are discussed in more detail with reference to FIGS. 3-9. The calibration phase 110 typically includes evaluating a plurality of calibration wafers, typically three or more, that are created for the calibration phase. The calibration wafers generally have a porous film or other dielectric layer deposited on a suitable substrate (e.g., silicon substrate). Other semiconductors, such as GaAs, InP, or SiC, may also be used, or any other materials like quartz or ceramics or glass may also be suitable for the substrate. The following description will focus on wafers with a silicon substrate and silicon dioxide porous layers, but the method can be used with any other dielectric material on any other substrate material.

The calibration phase includes measuring actual values of the property of interest of the dielectric material on calibration wafers using a known technique. In many cases, the dielectric layers on the calibration wafers can intentionally be formed to provide values for the DC (or RF) dielectric constant "k," Young's Modulus "M" and/or hardness "H" that range from minimum to maximum values. This can be performed by intentionally un-tuning the process of fabrication of the porous layer. The minimum-to-maximum interval should cover the normal variation of the fabrication process for the dielectric material. The dielectric constant "k" could be measured, for example, by an Hg probe or by a Q-V technique at the electrical frequency of interest (i.e., the frequency at which the device operates—typically in the kHz-GHz domain). The Young's Modulus and hardness can be measured by a mechanical method, such as nano-idents. These properties can also, at least to some extent, be measured indirectly by acoustic wave spectroscopy.

The calibration phase 110 also includes obtaining an IR spectrum for each calibration wafer. The IR spectrum for each sample can be obtained using FTIR or IR-SE as described above.

The calibration phase 110 further includes measuring the thickness of the dielectric layer on the individual calibration wafers. The thickness of the dielectric layers can be measured using VIS-Ellipsometry, FTIR, or IR-SE with an appropriate analysis algorithm (e.g., a model-based algorithm). After measuring the thickness of the dielectric layers and the IR spectrum from the individual calibration wafers, the calibration phase 110 continues by determining the correlation between IR spectra and the property of interest of the dielectric layers. One aspect of several embodiments of the invention is to determine a metric from the actual values of the property of interest, the test IR spectra, and the thicknesses of the dielectric material on the individual calibration wafers that accurately relates the measured IR spectrum from a process workpiece with a value of the property of the dielectric material.

a. Sum of Weighted IR Bands

One method for determining the metric between the value of interest for the dielectric layer and the IR spectra is a process involving summing weighted IR bands from the IR spectra of the calibration wafers. For purposes of this description, the property of interest is the RF (1 KHz) dielectric constant "k," and the IR spectra are collected using FTIR. If the spectra are collected by an IR spectral ellipsometer (IR-SE), the extinction coefficient spectrum or the imaginary part of the dielectric function spectra need to be calculated by simulating and fitting the experimental spectra. If the spectra are collected in reflection mode by an IR-spectrometer, the spectra can be used if they clearly show the absorption bands of the porous dielectric layer. If not, the same simulation-and-fit approach described above for the IR-SE spectra may need to be used for spectra collected in the reflection mode.

Figure 4:
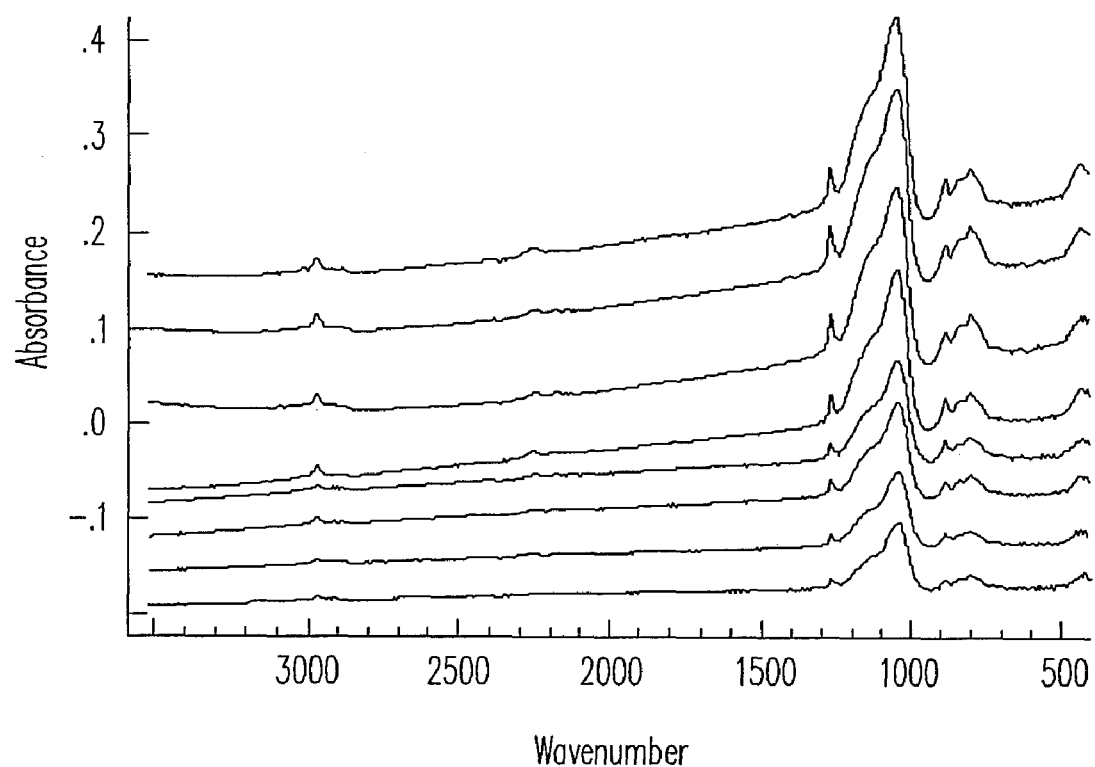
FIG. 4 is a graph of IR spectra from a plurality of corresponding calibration wafers at one stage of a calibration phase in accordance with a method of an embodiment of the invention.

FIG. 4 illustrates spectra collected by FTIR in transmission mode for a plurality of calibration wafers in accordance with one example. Additionally, Table 1 sets forth the values of the RF dielectric constant (k) and the thickness T corresponding to the FTIR spectra of the individual calibration wafers shown in FIG. 4. The dielectric values were measure by an Hg probe, and the thickness was measured by VIS-ellipsometry.

TABLE 1

| Sample | "k" | T (microns) |
|---|---|---|
| 1 | 3.0800 | 0.18406 |
| 2 | 2.7776 | 0.22267 |
| 3 | 2.6544 | 0.29932 |
| 4 | 2.1280 | 0.60624 |
| 5 | 2.6880 | 0.31281 |
| 6 | 2.5536 | 0.58856 |
| 7 | 2.8224 | 0.46480 |
| 8 | 2.9084 | 0.57328 |

Figure 5:
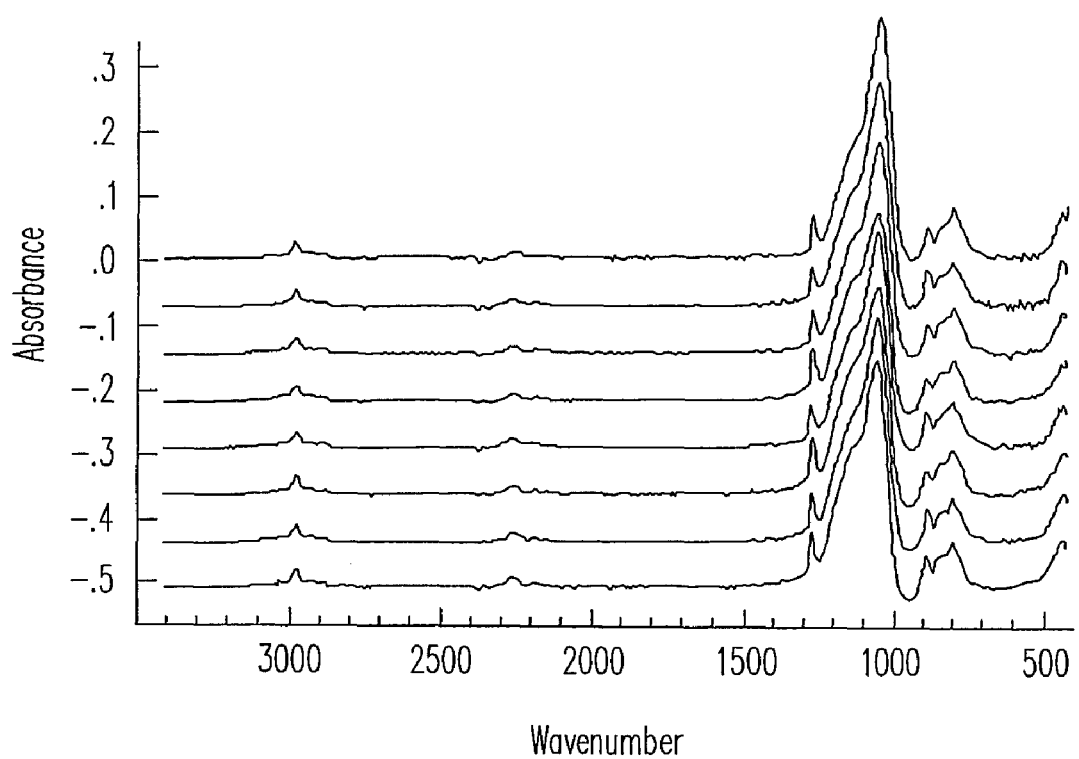
FIG. 5 is a graph illustrating the IR spectra of FIG. 4 after correcting the baseline and normalizing the IR spectra.

The calibration phase 110 can further include correcting the baseline and normalizing the IR spectra for the individual calibration wafers. In general, the baseline of an IR spectrum is not flat (e.g., the IR spectra illustrated in FIG. 4), and this can be corrected by mathematically manipulating the IR spectrum using well-known techniques for IR spectroscopy. Examples of baseline correction techniques are spline baseline correction, linear baseline correction, and Fourier-filter baseline correction. If the IR spectra are the extinction coefficient or the imaginary part of the dielectric function resulting from a simulation-and-fit approach, there is no need for a baseline correction. The IR spectra can be normalized by dividing each spectrum by the thickness T of the respective dielectric layer on the corresponding calibration wafer. FIG. 5 illustrates the IR spectra of FIG. 4 after correcting the baseline and normalizing the IR spectra.

Figure 6:
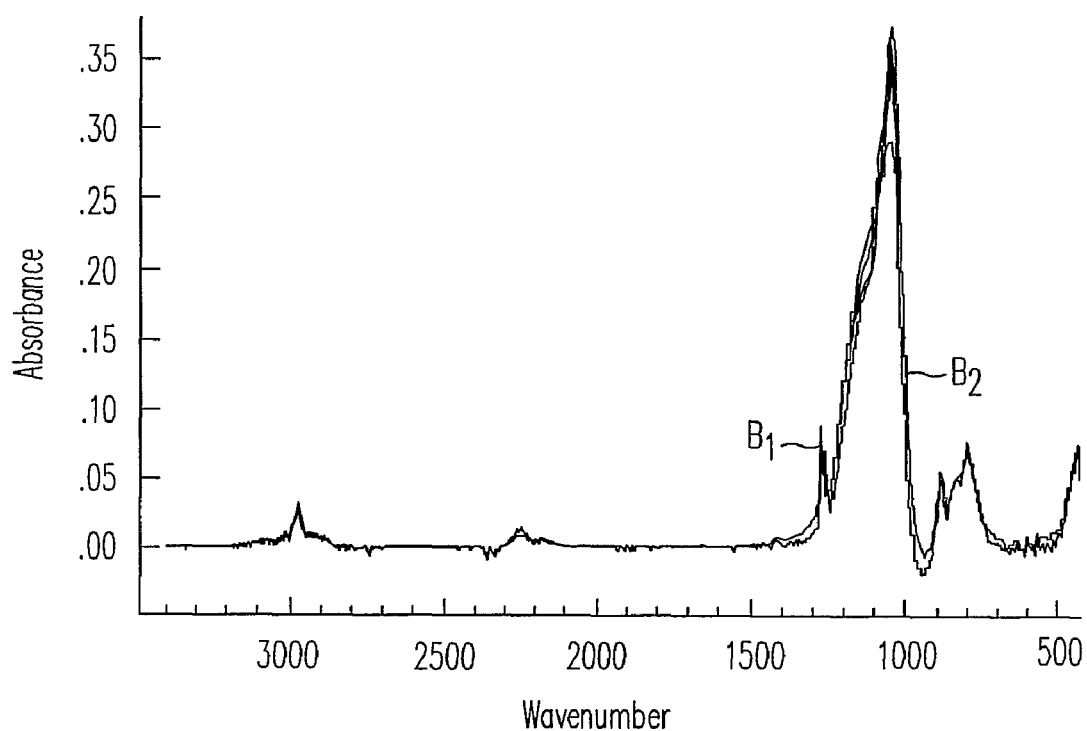
FIG. 6 is a graph in which the spectra illustrated in FIG. 5 are superimposed together to identify IR bands of interest.

FIG. 6 illustrates a subsequent step in the calibration phase 110 in which specific IR bands are selected and measured. The spectra illustrated in FIG. 5 are superimposed together to identify the IR bands that change with changes in the RF dielectric constant. The bands with the highest variation are typically selected to be used in subsequent steps of the calibration phase 110. This can be automatically performed by the computer 40 using the variance of all the spectra according to equation Eq. 1.

$$\text{Var}(v) = \sum_{i}^{NumSpectra} [Spectrum_i(v) - \langle Spectra(v) \rangle]^2 \quad \text{(Eq. 1)}$$

In the example shown in FIG. 6, a first band $B_1$ and a second band $B_2$ can be selected as having high variations in the spectra with variances of the RF dielectric constant. In actual applications, more than two bands can be selected.

Figure 7:
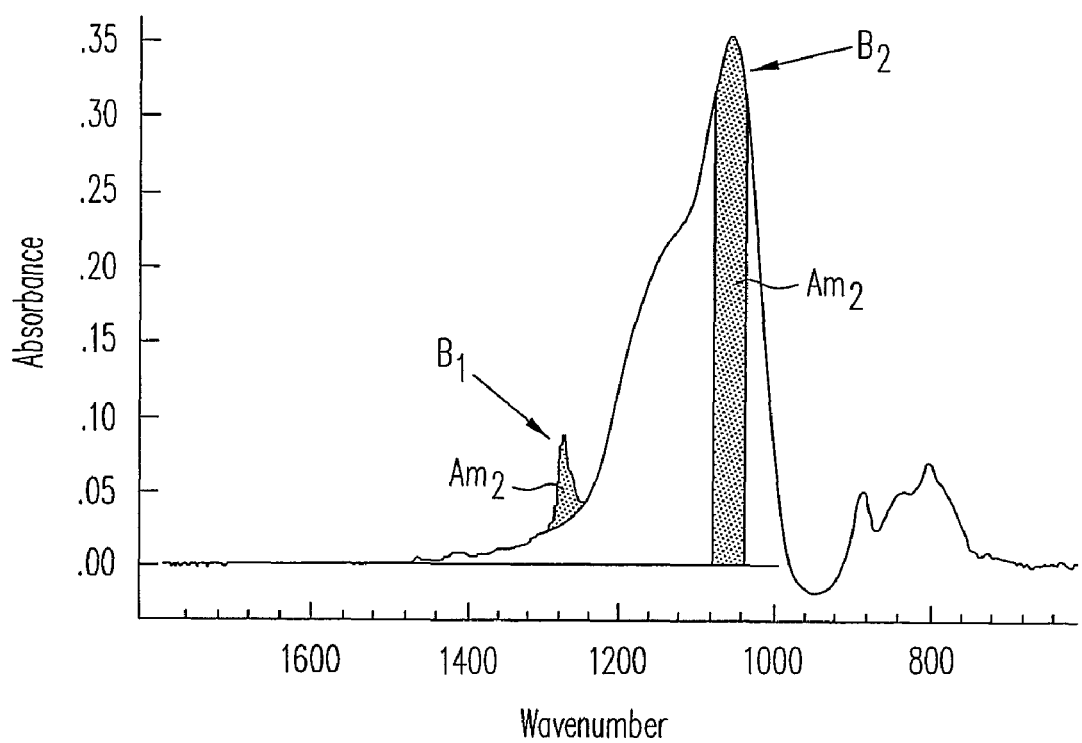
FIG. 7 is a graph illustrating measuring a portion of selected IR bands of the superimposed IR bands illustrated in FIG. 6.

After selecting the IR bands, the calibration phase 110 continues by measuring the intensity or area of the bands. FIG. 7 illustrates a measurement of the area $A_{m1}$ of the first band $B_1$ and the area $A_{m2}$ of the second band $B_2$. As shown in FIG. 7, a local baseline correction may be implemented to measure the band intensity or area of the individual bands.

In this embodiment of the method 100, the calibration phase 110 further includes creating a metric X by a sum of weighted bands. For example, the area or intensity of individual selected bands $A_{m1}$, where 1 refers to the particular band and m refers to the particular spectrum, is now weighted by a constant $w_1$. The metric X for each spectrum "m" is created by summing all of the weighted bands according to equation Eq. 2.

$$X_m = \sum_{l}^{IRbands} A_{ml} w_l \quad \text{(Eq. 2)}$$

The weights $w_1$ are adjusted by a regression or optimization routine (for example, Least-Squares, Levenberg-Marquardt, Trust-Region-Dogleg method, etc.) to produce a sufficient correlation between the known values of "$k_m$" for each spectrum "m." The formula to be regressed can be linear or quadratic or more generally polynomial of degree "n." In other embodiments, any suitable procedure that generates a high correlation with the "$k_m$" values can be used. Some analytical formulas—linear, quadratic and polynomial—are given here below in the equations of Eq. 3.

Linear correlation: $k_m = c_1 X_m + c_0$

Quadratic correlation: $k_m = c_2 X_m^2 + c_1 X_m + c_0$

Polynomial correlation: $k_m = c_n X_m^n + c_{n-1} X_m^{n-1} + \ldots + c_2 X_m^2 + c_1 X_m + c_0$ (Eq. 3)

where the factors $c_n, c_{n-1}, \ldots, c_2, c_1, c_0$ are constants.

Figure 8:
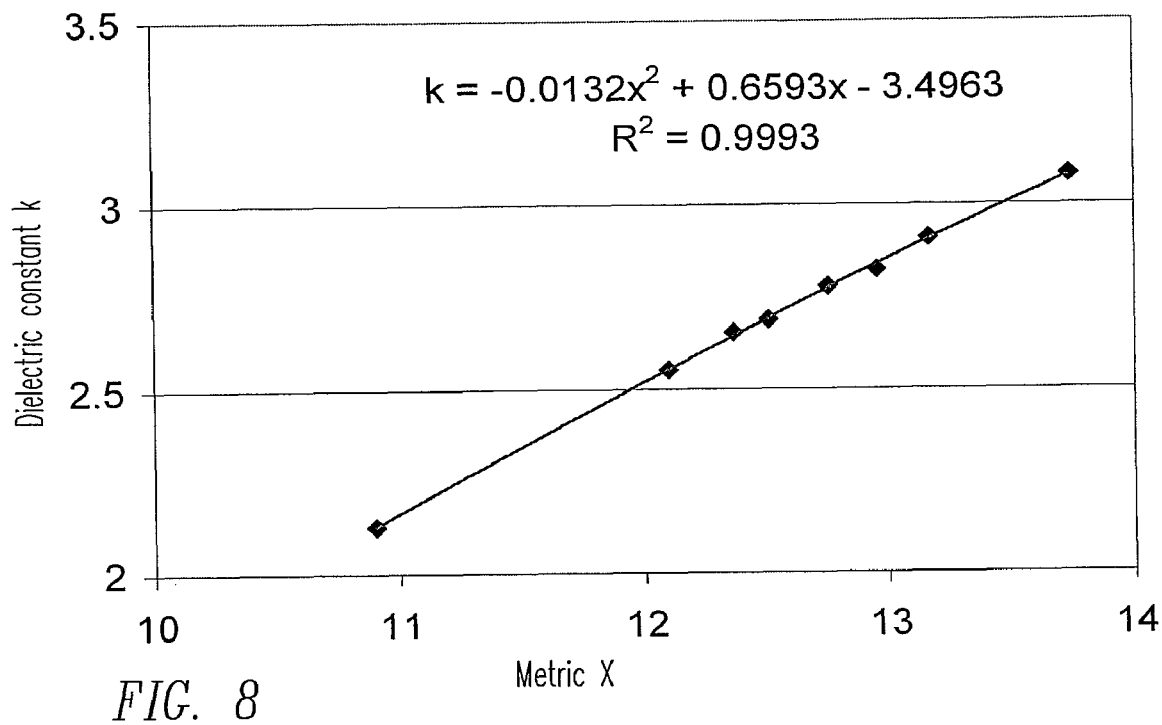
FIG. 8 is a plot of a metric X versus a RF dielectric constant k determined according to a calibration phase in accordance with an embodiment of the invention.

In the example of bands $B_1$ and $B_2$ shown in FIG. 7, a constant $w_1$ for the first band $B_1$ and a constant $w_2$ for the second band $B_2$ are both initially set to equal 1. The metric $X_m = A_{m1} w_1 + A_{m2} w_2$ was applied to each spectrum, and a quadratic regression was used. The weights $w_1$ and $w_2$ were adjusted in a Levenberg-Marquardt automization routine to find the best values for the metric X. In the case of the calibration wafers in the example from Table 1 and FIG. 7, $w_1$ equals 0.04937 and $w_2$ equals 0.95063 such that $X = 0.04937 \cdot A_1 + 0.95063 \cdot A_2$, and an equation solving the RF dielectric constant k as a function X was found to be $k = -0.0132 \cdot X^2 + 0.6593 \cdot X - 3.4963$. FIG. 8 is a plot of these correlations that shows this specific example achieves a correlation coefficient $R^2$ of 0.9993.

An example of the measurement stage 120 and determination stage 140 for a process workpiece with a dielectric layer that corresponds to those tested in the calibration wafers from Table 1 and FIG. 7 involves irradiating the process workpiece with an IR beam according to the same spectroscopic technique used to determine the IR spectra of the calibration wafers. The Transmission IR spectrum from the workpiece is then collected and the areas $A_1$ and $A_2$ corresponding to the bands $B_1$ and $B_2$ of the measured IR spectrum from the process workpiece are determined. The values for $A_1$ and $A_2$ from the collected measured IR spectrum is then input into the formula for X, which is then input into the equation for the RF dielectric constant k to output the dielectric constant for the RF dielectric layer on the process workpiece.

b. Sum of Curve-Fitted Weighted Bands

Another embodiment of the calibration phase 110 determines the correlation by obtaining a sum of weighted IR bands using band curve fitting. This embodiment is a variation of the previous embodiment of summing weighted IR bands, and all of the steps except the step of measuring the IR bands are the same. In this embodiment, a curve is fitted to each selected IR band. The curve can be a Gaussian function, a Lorentzian function, or a superposition of several Gaussian and/or Lorentzian functions. Other curves that can also be used are a Voigt function and/or a Pearson VII function. The selection of the curve type is performed on a trial-and-error basis, and all of the curves are tested for the best fit in a given IR band. The curve with the best fit for a given IR band is retained for subsequent steps regarding the specific IR band.

The curves can be represented by analytical mathematical expressions. For example, the analytical mathematical expression for the curves can be one or more of the equations in Eq. 4.

$$\text{Gaussian: } G(v, \alpha, \gamma) = \alpha \cdot e^{-\left(\frac{v-v_0}{\gamma}\right)^2 \ln(2)} \quad \text{(Eq. 4)}$$

$$\text{Lorentzian: } L(v, \alpha, \gamma) = \frac{\alpha}{\left(\frac{v-v_0}{\gamma}\right)^2 + 1}$$

$$\text{Voigt: } V(v, \alpha, \gamma_1, \gamma_2) = G(v, \alpha, \gamma_1) \otimes L(v, \alpha, \gamma_2)$$

$$\text{Pearson VII: } P(v, \alpha, \gamma) = \frac{\alpha}{\left[\left(2^{\frac{1}{M}} - 1\right)\left(\frac{v-v_0}{\gamma}\right)^2 + 1\right]^M}$$

$$\text{Mixed Gauss-Lorentz: } M(v, \alpha, \beta, \gamma) = \beta \cdot G(v, \alpha, \gamma) + (1-\beta) L(v, \alpha, \gamma)$$

In the analytical mathematical expressions for the curves listed above, $v$, $\alpha$ and $\gamma$ are respectively the wavenumber, the height and the half-width at one-half of the height of the IR band. Also, $\gamma_1$ and $\gamma_2$ are respectively the half-width at one-half height of the Gaussian and Lorentz functions in the Voigt function. Additionally, $\otimes$ is the convolution operation and $\beta$ is the Gaussian contribution in the mixed Gauss-Lorentz function.

Figure 9:
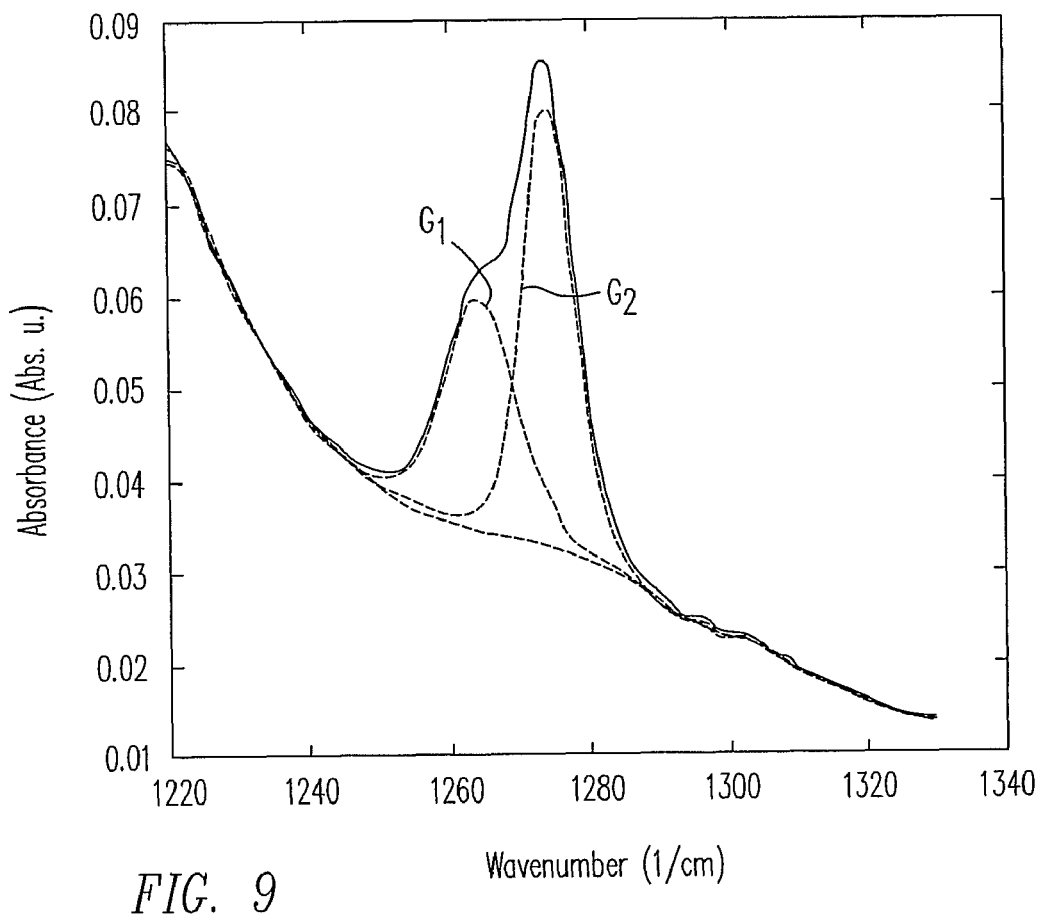
FIG. 9 is a graph illustrating a curve-fitting procedure for a selected IR band in accordance with another embodiment of the calibration phase.

Once the analytical expression for the fitted curve of each band is determined, the height or area to be used in the construction of the metric X can be ascertained. FIG. 9 is an example using the band $B_2$ from FIG. 7. Band $B_2$ was locally baselined by a spline function and then fitted by a superposition of two Gaussian functions $G_1$ and $G_2$. The height of $B_2$ is given by maximum of $(G_1 + G_2)$ and the area by the integral of $(G_1 + G_2)$.

c. Inverse Least Squares

Another embodiment of the calibration phase 110 involves determining the metric X using an inverse least squares algorithm. In this embodiment, the measured IR spectrum is obtained, corrected for the baseline, and normalized as described above. The selection and measurement of the IR bands $A_\lambda$ can also be performed as describe above, or $A_\lambda$ can be the value of the IR spectrum at a particular wavelength $\lambda$. The metric X can then be calculated according to an inverse least squares algorithm. More specifically, let $A_{m\lambda}$ be the IR band at "$\lambda$" (or the IR spectra value at $\lambda$) from the $m^{th}$ spectrum of the calibration set, $k_m$ be the constant "k" associated with that calibration sample, and $P_\lambda$ be a constant for the given IR band at $\lambda$ (or to a wavelength $\lambda$) that satisfy equation Eq. 5. $E_0$ is also a constant.

$$k_m = E_0 + \sum_\lambda A_{m\lambda} \cdot P_\lambda \quad \text{(Eq. 5)}$$

From a mathematical point of view, Eq. 5 can be solved when the number of selected IR bands "$\lambda$" (or wavelengths $\lambda$) is equal to the number of calibration samples plus one. Usually, the number of the calibration wafers is larger than that, and thus Eq. 5 must generally be solved in a "least squares" sense in order to obtain the values of $P_\lambda$ and $E_0$.

This approach can be generalized by using a more complex yet generic formula instead of Eq. 5. For example a polynomial formula as in Eq. 6 or any other mathematical formula that generates a good correlation with the values of "$k_m$" can be used.

$$k_m = E_0 + \sum_\lambda (P_{1,\lambda} \cdot A_{m,\lambda} + P_{2,\lambda} \cdot A_{m,\lambda}^2 + \ldots + P_{3,\lambda} \cdot A_{m,\lambda}^n) \quad \text{(Eq. 6)}$$

Once the parameters $P_{k,\lambda}$ and $E_0$ have been calculated from the calibration set, the metric X has the same formula as the one used to deduce those parameters.

d. Principal Components Regression

Another embodiment of the calibration phase 110 determines the metric using a Principal Components Regression (PCR). In this embodiment, the steps of obtaining the IR spectrum, correcting the baseline of the IR spectrum, and normalizing the IR spectrum are the same as those described above. In this embodiment, individual bands of the IR spectrum are not selected, but rather a spectral interval that contains IR bands which change according to the property to be measured (e.g., the RF dielectric constant k) is evaluated. For example, in the case of the calibration set presented in Table 1 and FIG. 7 above, it can be the interval of 700-1600 cm$^{-1}$. Alternatively, it could also be the entire spectrum.

In this embodiment, the metric is calculated by letting $A_{m\lambda}$ be the spectra value at wavelength $\lambda$ from the $m^{th}$ spectrum of the calibration set, and where $k_m$ is the constant "k" associated with that calibration sample. The PCR algorithm starts by decomposing the set of M calibration spectra into a reduced set of G(G<M) orthogonal artificial spectra by using the "Principal Components Analysis" technique. These artificial spectra, known as "PCA Factors," are ordered by degree of importance and have the property of being able to recreate any of the calibration spectra by linear combination, e.g., Eq. 7 is one such linear combination.

$$A_{m\lambda} = \varepsilon_{m\lambda} + \sum_g^G S_{mg} \cdot F_{g\lambda} \quad \text{(Eq. 7)}$$

In Eq. 7, $F_{g\lambda}$ is the $g^{th}$ factor (or artificial spectra) at the wavelength $\lambda$, and $S_{mg}$ is a constant known as "Score" that is the contribution of the PCA Factor "g" to recreate the spectrum $A_{m\lambda}$. The term $\varepsilon_{m\lambda}$ is known as residual spectrum and represents the difference between the measured spectrum and its reconstruction by the PCA Factors. The total number of factors (G), known as "PCA Rank," can be optimized such that the residual spectra is within the noise level of the measured spectra. The algorithm to calculate the PCA Factors and the optimum Rank is well described in the literature. Once the Factors and Scores are known for a given calibration set, PCR uses an inverse least squares algorithm to estimate "k" according to Eq. 8.

$$k_m = E_0 + \sum_\lambda S_{mg} \cdot P_g \quad \text{(Eq. 8)}$$

As in the previous section, this set of equations must be solved by "least squares" regression to get the coefficients $P_g$ and $E_0$ (and therefore the name "Principal Component Regression"). One advantage of using PCR is that there is no need to define the IR bands, and thus baseline correction can be avoided. Ultimately, the whole spectrum of each calibration sample can be used such that the large number of wavelengths introduces an averaging effect that reduces the noise impact.

As before, this approach can be generalized by using a more complex formula for the Eq. 8. For example, a polynomial formula as in Eq. 6 or any other mathematical formula that generates a good correlation with the values of "$k_m$." Once the parameters $P_g$ and $E_0$ have been calculated from the calibration set, the metric X has the exact same formula as the one used to deduce those parameters (e.g., Eq. 8).

e. Partial Least Squares

Still another embodiment of the calibration phase 110 involves determining the metric using a partial least squares algorithm. In this embodiment, the IR spectrum, baseline correction, and normalization can be performed as described above. The partial least squares algorithm is very similar to the principal components regression. The partial least squares algorithm calculates "Factors" and "Scores" from a calibration set, but unlike the principal components regression, the partial least squares Factors and Scores are deduced from the calibration spectra and the corresponding values for the RF dielectric constant k. The estimation of the values for the RF dielectric constant are a direct result from the reconstruction of the test IR spectrum from the partial least squares Factors and Scores. One advantage of using a partial least squares process over a principal components regression is that it results in a more robust calibration because the values for the RF dielectric constants of the calibration set are included in the construction of the Factors and Scores.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

What is claimed is:

1. A non-contact method for evaluating a property of a dielectric material on a microelectronic process workpiece, comprising:

measuring a thickness of the dielectric material on the workpiece;

irradiating the workpiece with a plurality of infrared (IR) wavelengths;

collecting and measuring an IR spectrum from the workpiece;

using the measured thickness and at least a portion of the measured IR spectrum of the workpiece and a predetermined correlation between the thickness of dielectric material, IR spectra and at least one of a dielectric constant, the hardness, and Young's Modulus to determine at least one of the dielectric constant, the hardness, and Young's Modulus of the dielectric material; and storing and/or displaying a value of the determined at least one of the dielectric constant, the hardness, and Young's Modulus for the dielectric material of the workpiece.

2. The method of claim 1, wherein irradiating the workpiece and collecting and measuring an IR spectrum is performed using one of an IR spectrometer and an Infrared Spectral Ellipsometer.

3. The method of claim 1, wherein measuring a thickness of the dielectric material is performed using one of an IR spectrometer and an Infrared Spectral Ellipsometer.

4. The method of claim 1, wherein the collected and measured IR spectrum is at least one of a transmission IR spectrum, reflection spectrum and an Ellipsometric spectrum.

5. The method of claim 1, wherein the predetermined correlation is produced empirically.

6. The method of claim 5, wherein producing the predetermined correlation comprises:
   providing a plurality of the calibration wafers with dielectric material each having a known thickness for the dielectric material and known values of at least one of the dielectric constant, the hardness, and Young's Modulus for the dielectric material;
   collecting a test IR spectrum from each calibration wafer to obtain a plurality of test IR spectra;
   determining a metric from the known thicknesses, the known values of at least one of the dielectric constant, the hardness, and Young's Modulus for the dielectric material, and the test IR spectra, wherein the metric relates the measured IR spectrum with a value of at least one of the dielectric constant, the hardness, and Young's Modulus for the dielectric material.

7. The method of claims 6, wherein determining the metric further comprises performing a baseline correction of the test IR spectrum of the calibration wafers and normalizing the baseline corrected test IR spectra by dividing the individual test IR spectrum by the corresponding thickness of the individual dielectric material.

8. The method of claim 6, wherein determining the metric further comprises:
   selecting a plurality of IR bands from the test IR spectra;
   determining a weighting factor for individual IR bands; and
   summing products of the weighting factors and areas of corresponding IR bands from the test IR spectra.

9. The method of claim 8, further comprising determining an equation that correlates the values of the metric to values of at least one of the dielectric constant, the hardness, and Young's Modulus for the dielectric material.

10. The method of claim 9, further comprising:
   summing the products of the weighting factors and areas of corresponding IR bands of the measured IR spectrum to determine a value of the metric for the dielectric layer of the workpiece; and
   inputting the determined value of the metric for the dielectric layer of the workpiece into the equation that correlates the values of the metric to values of at least one of the dielectric constant, the hardness, and Young's Modulus for the dielectric material.

11. The method of claims 8, further comprising fitting a curve to the selected IR bands.

12. The method of claim 11 wherein fitting a curve to the selected IR bands comprises fitting a sum of Gaussian functions and/or a Lorentzian functions to the selected IR bands.

13. The method of claims 6 wherein determining the metric comprises performing one of an inverse least squares computation, a partial least squares computation, and a principal components regression computation.

14. A method of generating a correlation factor for evaluating a property of a dielectric material on a process workpiece, in which the thickness of the dielectric material and a response infrared (IR) spectrum from the workpiece are used with the correlation factor to determine at least one of the dielectric constant, the hardness, and Young's Modulus of the dielectric material, the method of generating the correlation factor comprising:
   providing a plurality of the calibration wafers with the dielectric material;
   measuring a value of the at least one of the dielectric constant, the hardness, and Young's Modulus of the dielectric material on individual calibration wafers;
   measuring a thickness of the dielectric material on the individual calibration wafers;
   collecting a test IR spectrum from individual calibration wafers to obtain a plurality of test IR spectra;
   determining a metric from the measured values for the individual calibration wafers, the thicknesses of the dielectric material on the individual calibration wafers, and the test IR spectra, wherein the metric relates the measured IR spectrum with a value of at least one of the dielectric constant, the hardness, and Young's Modulus of the dielectric material;
   storing the metric as the correlation factor.

15. The method of claim 14, wherein the test IR spectrum is collected using an IR spectrometer or an IR spectral Ellipsometer.

16. The method of claims 14, wherein determining the metric further comprises performing a baseline correction of the test IR spectrum of the calibration wafers and normalizing the baseline corrected test IR spectra by dividing the individual test IR spectrum by the corresponding thickness of the individual dielectric material.

17. The method of claim 14, wherein determining the metric further comprises:
   selecting a plurality of IR bands from the test IR spectra;
   determining a weighting factor for individual IR bands; and
   summing products of the weighting factors and areas of corresponding IR bands from the test IR spectra.

18. The method of claim 17, further comprising determining an equation that correlates the values of the metric to values of at least one of the dielectric constant, the hardness, and Young's Modulus for the dielectric material.

19. The method of claim 18, further comprising:
   summing the products of the weighting factors and areas of corresponding IR bands of the measured IR spectrum to determine a value of the metric for the dielectric layer of the workpiece; and
   inputting the determined value of the metric for the dielectric layer of the workpiece into the equation that correlates the values of the metric to values of at least one of the dielectric constant, the hardness, and Young's Modulus for the dielectric material.

20. The method of claim 17, further comprising fitting a curve to the selected IR bands.

21. The method of claim 20 wherein fitting a curve to the selected IR bands comprises fitting a sum of Gaussian functions and/or a Lorentzian functions to the selected IR bands.

22. The method of claims 14 wherein determining the metric comprises performing one of an inverse least squares computation, a partial least squares computation, and a principal components regression computation.

* * * * *